United States Patent [19]

Weber et al.

[11] Patent Number: 4,940,818

[45] Date of Patent: Jul. 10, 1990

[54] PROCESS ON THE PREPARATION OF 2,2′-OXYBIS(N,N-DIMETHYL-ETHANA-MINE)

[75] Inventors: Jürgen Weber, Oberhausen; Detlef Kampmann, Bochum; Franz Thönnessen; Claus Kniep, both of Oberhausen, all of Fed. Rep. of Germany

[73] Assignee: Hoechst Aktiengesellschaft, Werk Ruhrchemie, Fed. Rep. of Germany

[21] Appl. No.: 210,634

[22] Filed: Jun. 23, 1988

[30] Foreign Application Priority Data

Jun. 30, 1987 [DE] Fed. Rep. of Germany ....... 3721538

[51] Int. Cl.$^5$ .............................................. C07C 85/02
[52] U.S. Cl. .................... 564/471; 564/472; 564/473; 564/474
[58] Field of Search ................ 564/471, 472, 473, 474

[56] References Cited

U.S. PATENT DOCUMENTS

| 3,136,819 | 6/1964 | Shapiro | 260/583 |
| 4,621,158 | 11/1986 | Hubert et al. | 564/471 |

FOREIGN PATENT DOCUMENTS

| 6454 | 1/1980 | European Pat. Off. . | |
| 115071 | 8/1984 | European Pat. Off. . | |
| 0142868 | 5/1985 | European Pat. Off. | 564/471 |
| 1932422 | 1/1971 | Fed. Rep. of Germany | 564/471 |

Primary Examiner—Richard L. Raymond
Assistant Examiner—Raymond Covington
Attorney, Agent, or Firm—Bierman & Muserlian

[57] ABSTRACT

A process for the preparation of 2,2′-oxybis[N,N-dimethylethanamine] by reaction of 2,2′oxybisethanamine, hydrogen and formaldehyde having a reduced percentage of water on conventional fixed-bed hydrogenation catalysts. The reactants, especially the amine and formaldehyde, are heated to a predetermined temperature separate from each other, and then mixed with each other in the presence of the fixed-bed catalyst.

18 Claims, No Drawings

PROCESS ON THE PREPARATION OF 2,2'-OXYBIS(N,N-DIMETHYL-ETHANAMINE)

This Application claims the priority of German Application P 37 21 538.8, filed Jun. 30, 1987.

The present invention relates to a process for the preparation of 2,2'-oxybis[N,N-dimethylethanamine]. This product—also called bis-[2-(N,N-dimethylamino)ethyl] ether—is an industrially important compound, useful as a polymerization, curing and foaming catalyst for the manufacture of epoxy-based plastic and especially urethane based plastics.

The compound 2,2'-oxybis[N,N-dimethylethanamine] can be synthesized in various known ways. U.S. Pat. No. 4,247,482 teaches that N,N-dimethylethanolamine is treated with gaseous sulfur trioxide and 63 to 68% bis[2-(N,N-dimethylamino)ethyl] ether is obtained, water being split off. U.S. Pat. No. 3,400,157 describes the reaction of bis(2-chloro-ethyl) ether dissolved in water with dimethylamine used in excess. The desired ether is liberated by the addition of aqueous alkali. The yield is 66% of bis-[2-N,N-dimethylamino)ethyl] ether based on the bis(2-chloroethyl) ether.

According to DE 28 24 908, dimethylamine, diethylene-glycol and hydrogen as starting materials are reacted on a fixed-bed copper catalyst under pressure and at elevated temperature in the liquid phase. If the unreacted starting materials and the dimethylaminoglycol ether formed during the reaction are recycled directly to the synthesis, a mixture with 60 wt. % tetramethylbis(aminoethyl) ether and (bis-[2-N,N'-dimethylamino)ethyl] ether is obtained.

The processes described above are, on the one hand, highly complicated and, on the other hand, produce a relatively low yield of the desired product. Therefore, there is a demand for a process which is both simple to perform and produces the desired ether (2,2'-oxybis(N,N'-dimethylethanamine) in high yield.

These requirements are satisfied by a process for the preparation of 2,2'-oxybis[N,N-dimethylethanamine] by the reaction of an amine, an oxygen-containing compound, and hydrogen as starting materials under pressure and at elevated temperature, preferably in the liquid phase and on a fixed-bed catalyst. 2,2'-oxybisethanamine is used as the amine, formaldehyde as the oxygen-containing compound, the fixed-bed catalyst is a hydrogenation catalyst containing Ni, Cu, Co, Mn, Fe, Rh, Pd and/or Pt, and the starting materials, in particular the formaldehyde, contain a reduced percentage of water. The starting materials, formaldehyde and hydrogen, are substances produced on an industrial scale. The 2,2'-oxybisethanamine (bis-(2-aminoethyl) ether) is also readily available as it always occurs as a by-product in the manufacture of morpholine from ethanolamine.

The bis-(2-aminoethyl) ether, formaldehyde, and hydrogen are reacted at 0.1 to 30, preferably 1 to 20 and most preferably, 2 to 15 MPa. The reaction temperature is 20° to 250°, preferably 50° to 200° and, most preferably, 70° to 150° C. The process according to the invention can be operated discontinuously or continuously and proceeds according to the following equation:

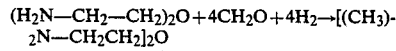

Such a reaction is also called hydrogenating N-methylation of the amine. A summary of this type of process is to be found in Houben-Weyl, Methoden der organischen Chemie; Volume XI/1, pages 641 to 647, 4th edition (1957).

The standard hydrogenation catalysts containing Ni, Co, Cu, Mn, Fe, Rh, Pd and/or Pt can be used as the fixed-bed catalyst. The pressure and temperature are, to a certain extent, dependent on the type of catalyst and must be selected accordingly. An important factor for the success of the process according to the invention is that the starting materials—in particular the formaldehyde and thus the mixture present in the reactor—have a reduced percentage of water.

Too high a percentage of water is undesirable as it damages the fixed-bed catalyst. On the one hand, it impairs the activity of the catalyst and reduces both conversion and selectivity; on the other hand, it leads to rapid decomposition of the fixed-bed catalyst. A reduction of the percentage of water in the starting materials helps to avoid this disadvantage.

The process according to the invention has several advantages: Firstly, it is based on readily available starting materials, secondly, it is easy to carry out. Thirdly, it permits the use of standard hydrogenation catalysts, thus making it possible to flexibly adapt the process to the prevailing plant conditions and, fourthly, it produces the desired end product almost without the formation of undesired by-products. Thus, the conversion is 99 to 100% and the selectivity 96 to 99.5% based on the 2,2'-oxybisethanamine used. The reaction mixture contains the 2,2'-oxybis[N,N-dimethylethanamine] in an amount corresponding to a yield of 95 to 99.5%.

However, it is generally not possible to transfer the results of the discontinuous (batch) tests to a continuous reaction with formaldehyde and hydrogen. This is especially true of 2,2'-oxybisethanamine[bis(2-aminoethyl)ether] (hereinafter the amine). There are various reasons for this.

Continuous N-methylation pressure-resistant tubular reactors which contain the hydrogenation catalyst in lump form are normally used. The starting materials (or their reaction mixtures) are fed into the reactor either at the head or the bottom; depending on the type of feed, one speaks of trickling or bottom phase operation. When used over a prolonged period, the hydrogenation catalysts decompose to an increasing degree. The resultant fine particles lead to fouling either in the tubular reactors or in the downstream plant sections. This leads to an increase in pressure in the reaction apparatus which means that the reaction has to be stopped to permit clearing of the blockage.

The pressure of formic acid, which probably forms from formaldehyde through the Cannizzaro reaction, is also undesirable. It removes a corresponding amount of amine from the reaction in the form of a salt. The free acid and the amine salt both promote corrosion of the reactor system.

Another side reaction impairing continuous reaction is a result of the polymerization of formaldehyde and the polycondensation between the amine and formaldehyde to hexahydrotriazines. In the case of multivalent amines, this leads to the formation of higher molecular weight compounds. This causes the catalyst charge to become sticky and, therefore, tends to block the reactor. Here, too, the unavoidable result is the necessity of frequent changing of the catalyst.

Another important factor in continuous operation is that the starting materials are heated to a predetermined temperature separately from each other and then mixed together in the presence of the fixed-bed catalyst. This means that the amine, formaldehyde, and hydrogen are passed through their own lines and heated before they are reacted. However, the hydrogen can also be mixed with either the amine or with formaldehyde, then preheated, and fed into the reaction. It is also possible to spread the hydrogen over the amine and the formaldehyde. According to a particularly preferred embodiment of the invention, the hydrogen is mixed with the amine and heated.

On the other hand, it is not acceptable to mix and heat the amine and formaldehyde before the reaction takes place. The amine and formaldehyde must always be kept separate from each other and heated to the predetermined temperature before they are reacted in the presence of the fixed-bed catalyst. If the materials are mixed before entering the catalyst zone, caking and sticking of the fixed-bed catalyst will occur within a very short time, probably as a result of polymerization reactions. Thus, the pressure reactor will become clogged due to blockages and the reaction will have to be stopped for cleaning and possible catalyst replacement.

Furthermore, it must be insured that the percentage of water in the reaction is limited. This is achieved by using starting materials with reduced percentages of water. The amine exhibits only minor or trace amounts of water. On the other hand, the standard commercial formaldehyde usually contains approximately 60% or more water by weight. In addition to the water which is brought into the reaction with the starting materials, there is also the water which is formed during the course of reaction. The total amount of water should not exceed 50% by weight based on the liquid-gas mixture flowing around the fixed-bed catalyst.

It is particularly expedient to limit the water content of the formaldehyde solution. Preferably, it should not exceed 50% by weight based on the total formaldehyde solution. Formaldehyde solutions with 0 to 50% water by weight are suitable. Those with 5 to 30% water by weight are preferred, and a formaldehyde with 7 to 15% water by weight is most preferred. Paraformaldehyde can also be successfully used; e.g., in suspended form.

The amine and/or the formaldehyde can be added after being dissolved in a solvent. Particularly suitable solvents are aliphatic alcohols with 1 to 5 carbon atoms, ethers such as tetrahydrofurane and dioxane, dimethylsulfoxide, and mixtures thereof.

The predetermined temperature depends primarily on the reaction temperature. It should not be more than 20°, preferably not more than 10° and, most preferably, not more than 5° C., below the reaction temperature. Moreover, it should not be more than 10°, preferably not more than 5° and, most preferably, not more than 0° C. above the reaction temperature. Most advisable is a temperature range of 20° to 0°, preferably 10° to 0° and, most preferably, 5° to 0° C. below the reaction temperature.

After the starting materials have been heated to the preset temperature, they are mixed together in the presence of the fixed-bed catalyst. It is desirable that all three starting materials—amine, formaldehyde and hydrogen—only come into contact with each other in the presence of the fixed-bed catalyst.

However, if the hydrogen is added to the reaction together with one of the other starting materials, the amine and the formaldehyde must only contact each other in the presence of the fixed-bed catalyst. In this case as well, all three of the starting materials only come into contact with each other in the presence of the catalyst. In engineering terms this requirement is met by terminating the pipe or the pipe system carrying either the amine or the formaldehyde in the catalyst zone. This insures that these starting materials only come into contact with each other in the presence of the catalyst. According to a preferred embodiment of the invention, the pipe carrying the formaldehyde terminates in the catalyst zone.

However, it is also possible to have the pipes of two or even all three starting materials terminating in the zone of the fixed-bed catalyst. The arrangement of the pipes to be chosen will depend on the amounts of starting materials, geometry of the catalyst zone, and the required flow ratios. If the throughputs of the substances are to be substantial per unit time, it is recommended that several pipes be used for each starting material. Should the flow ratios not ensure sufficient mixing of the reactants in the catalyst zone, additional distribution devices are useful. These devices can, for example, be mounted as ring showers or shower heads at the end of the pipe. However, other distributor systems such as nozzles, frits, or pipe bundles can also be used.

The process according to the invention is not restricted to the use of special catalysts but permits the use of a large number of conventional fixed-bed catalysts. The fixed-bed catalysts can be either supported or support-free. They contain Ni, Co, Cu, Mn, Fe, Rh, Pd and/or Pt, preferably Ni, Co and/or Pd and, in addition, if desired, conventional additives and promoters; for example, alkaline earth oxides, $SiO_2$, $Al_2O_3$, $MnO_2$ and/or $Cr_2O_3$. The use of supported catalysts is advantageous. $Al_2O_3$, $SiO_2$, silica gel, kieselguhr, activated carbon and pumice stone are particularly useful.

It is particularly desirable to use catalysts with 10 to 75, preferably 20 to 70 and, most preferably, 40 to 65 wt. % Ni, Co, Cu, Mn and/or Fe based on the total catalyst mass.

Noble metal catalysts permit reaction under particularly mild conditions. They are customarily supported and have a metal content of 0.1 to 20, preferably 0.2 to 15 and, most preferably, 0.5 to 10 wt. % based on the total catalyst mass. Suitable noble metals are Rh, Pd and/or Pt. Shaped materials based on $Al_2O_3$, $SiO_2$, activated carbon, silica gel, kieselguhr and/or pumice stone are recommended as supports.

The catalyst determines the reaction conditions, in particular the reaction temperature and the pressure. For best results, Ni, Co, Cu, Mn and/or Fe-containing base metal catalysts require temperatures of 50° to 250°, preferably 70° to 200°, and, most preferably, 100° to 150° C. and pressures of 3 to 30, preferably 5 to 20 and, most preferably, 8 to 15 MPa.

Noble metal catalysts are best used at temperatures of 20° to 165°, preferably 30° to 160° and, most preferably, 50° to 150° and pressures of 0.1 to 15, preferably, 0.2 to 12 and, most preferably, 0.5 to 10 MPa. Particularly mild conditions are provided by temperatures of up to 100° C. A more rapid reaction takes place at temperatures ranging from 100° to 165°, preferably 110° to 160° and, most preferably, 115° to 150° C.

Per mol of amine, 4 to 8 mols of formaldehyde are added. Preferably, 4 to 6 moles per mole of amine are used. Most preferred is 4 to 4.8 moles of formaldehyde per mol of amine. Per mol of formaldehyde, 1 to 10, preferably, 1.05 to 5 and, most preferably, 1.1 to 2.5 moles of $H_2$ are used.

EXAMPLES

The reactor vessel consists of a pressure-resistant pipe with an inside diameter of 28 mm. Raschig rings with a diameter of 3 mm are placed in the bottom of the pressure pipe to a height of 800 mm. This serves as a preheating zone in which the starting materials are heated to the predetermined temperature. The heating jacket surrounding the reactor is used for this purpose. The fixed-bed catalyst is located above the pre-heating zone.

The reactor is filled with bis(aminoethyl)ether at the beginning of the reaction. The starting materials are pumped into the bottom of the reactor, the reaction mixture is drawn off above the catalyst zone and passed to a pressure separator. The amine is fed into the reactor together with the hydrogen and flows through the pre-heating zone filled with the Raschig rings; the formaldehyde is pumped directly into the fixed-bed catalyst layer via a separate ascension pipe which passed through the pre-heating zone and is only mixed with the amine and hydrogen at the catalyst zone. The pre-heating zone and the starting materials are heated by means of the heating jacket surrounding the outside of the reactor to the desired predetermined temperature.

EXAMPLE 1

The reaction is performed continuously for 860 hours under the conditions listed in the following table. No complications occur. On completion of the reaction, the catalyst is withdrawn from the reactor to be examined. It exhibits neither signs of decomposition nor sticking and has maintained its activity.

COMPARATIVE EXAMPLE 1

Example 1 is repeated except that amine and formaldehyde are mixed together in the pre-heating zone and passed into the catalyst zone as a mixture. After only 20 hours, a sharp drop in the performance of the catalyst is already observed. After a total of 50 hours, the reaction has to be stopped due to clogging of the pressurized reactor resulting from polymer formation.

EXAMPLE 2

The reaction is performed continuously for 120 hours under the conditions listed in the following Table. There are no complications. On completion of the reaction, the catalyst is removed from the reactor for examination. It exhibits neither signs of decomposition nor sticking and has maintained its activity.

COMPARATIVE EXAMPLE 2

Example 2 is repeated except that the amine and formaldehyde are mixed together in the pre-heating zone and passed into the catalyst zone as a mixture. After only 35 hours, there is a sharp drop in performance of the catalyst. After a total of 90 hours, the reaction has to be stopped due to clogging of the pressurized reactor resulting from polymer formation.

TABLE

| Reaction conditions: | | |
|---|---|---|
| Predetermined temperature | 146 to 147° C. | 125 to 127° C. |
| Reaction temperature | 150° C. | 130° C. |
| Reaction pressure | 10 MPa | 10 MPa |
| Catalyst | 230 ml Ni 52/35* | 200 ml Pd/Al$_2$O$_3$** |
| Feed: | | |
| Bis(aminoethyl)ether | 35 ml/h | 30 ml/h |
| Formaldehyde*** | 65 to 70 ml/h | 60 to 65 ml/h |
| Composition of the reaction mixture: | | |
| Bis-[2-(N,N-dimethylamino)ethyl]ether | 51.2 wt. % | 50.7 wt. % |
| Water | 26.5 wt. % | 27.2 wt. % |
| Methanol | 20.1 wt. % | 20.4 wt. % |
| Miscellaneous | 2.2 wt. % | 1.7 wt. % |

*nickel-containing catalyst with 48 to 53% Ni by weight Ni based on the catalyst mass; the support material is kieselguhr, a product of Hoechst AG.
**palladium catalyst having 10% Pd by weight based on the catalyst mass; the support material is Al$_2$O$_3$
***formaldehyde solution (55% formaldehyde, 35% methanol, and 10% water, all by weight).

What we claimed is:

1. In a process for the preparation of 2,2'-oxybis-[N,N-dimethylethanamine] by reacting 2,2'-oxybisethanamine with an oxygen containing compound and hydrogen at an elevated temperature and pressure on a fixed-bed catalyst, the improvement comprising using as the oxygen containing compound, formaldehyde with not more than 50% by weight of water present in the reaction mixture, the formaldehyde and amine being heated to the elevated temperature before being mixed together and the fixed-bed catalyst is a hydrogenation catalyst selected from the group consisting of Ni, Co, Cu, Mn, Fe, Rh, Pd and Pt containing catalysts and a reduced amount of water.

2. The process of claim 1 wherein said reaction is carried out under a pressure of 0.1 to 30 MPa. and at a reaction temperature of 20° to 250° C.

3. The process of claim 2 wherein said pressure is 1 to 20 MPa. and said reaction temperature is 50° to 200° C.

4. The process of claim 3 wherein said pressure is 2 to 15 MPa. and said reaction temperature is 70° to 150° C.

5. The process of claim 1 wherein said formaldehyde is in solution.

6. The process of claim 5 wherein said solution contains 0% to 50% by weight of water.

7. The process of claim 6 wherein said solution contains 5% to 30% by weight of water.

8. The process of claim 7 wherein said solution contains 7% to 15% by weight of water.

9. The process of claim 2 wherein said reaction is carried out at a reaction temperature, said predetermined temperature being from 20° C. below said reaction temperature to 10° C. above said reaction temperature.

10. The process of claim 9 wherein said predetermined temperature is from 10° C. below said reaction temperature to 5° C. above said reaction temperature.

11. The process of claim 10 wherein said predetermined temperature is from 5° C. below said reaction temperature to 0° C. above said reaction temperature.

12. The process of claim 9 wherein said predetermined temperature is from 20° C. below said reaction temperature to 0° below said reaction temperature.

13. The process of claim 12 wherein said predetermined temperature is from 10° C. below said reaction temperature to 0° C. below said reaction temperature.

14. The process of claim 13 wherein said predetermined temperature is from 5° C. below said reaction temperature to 0° C. below said reaction temperature.

15. The process of claim 1 wherein said catalyst comprises Ni, Co, Cu, Mn, Fe, or mixtures thereof.

16. The process of claim 1 wherein said catalyst comprises Rh, Pd, Pt, or mixtures thereof.

17. The process of claim 1 wherein said catalyst is supported by a catalyst carrier taken from the class consisting of Al$_2$O$_3$, SiO$_2$, silica gel, kieselguhr, activated charcoal, pumice, and mixtures thereof.

18. The process of claim 1 wherein alkaline earth oxides, SiO$_2$, Al$_2$O$_3$, MnO$_2$, Cr$_2$O$_3$, and mixtures thereof are provided as additives and promoters.

* * * * *